US010995066B1

(12) United States Patent
Kwak et al.

(10) Patent No.: US 10,995,066 B1
(45) Date of Patent: May 4, 2021

(54) METHOD FOR PREPARING NOVEL CRYSTALLINE FORMS OF 1-(4-BENZYLOXY-BENZYL)-3-METHYL-THIOUREA

(71) Applicant: Therasid Bioscience Inc., Gyeonggi-do (KR)

(72) Inventors: Wooyoung Kwak, Gyeonggi-do (KR); Sungki Seo, Seoul (KR); Heung Jae Kim, Gyeonggi-do (KR)

(73) Assignee: Therasid Bioscience Inc., Gyeonggi-do (KR)

( * ) Notice: Subject to any disclaimer, the term of this patent is extended or adjusted under 35 U.S.C. 154(b) by 37 days.

(21) Appl. No.: 16/696,353

(22) Filed: Nov. 26, 2019

(51) Int. Cl.
C07C 335/12 (2006.01)
(52) U.S. Cl.
CPC ........ *C07C 335/12* (2013.01); *C07B 2200/13* (2013.01)
(58) Field of Classification Search
CPC .................................................. C07C 335/12
See application file for complete search history.

(56) References Cited

U.S. PATENT DOCUMENTS

| | | | | |
|---|---|---|---|---|
| 9,527,805 | B2 * | 12/2016 | Casero | C07D 209/48 |
| 10,407,388 | B2 * | 9/2019 | Lee | C07C 335/12 |
| 2018/0235912 | A1 * | 8/2018 | Lee | A61P 19/02 |
| 2018/0265462 | A1 * | 9/2018 | Lee | A61P 3/06 |

FOREIGN PATENT DOCUMENTS

KR         20160132534 A    * 11/2016

OTHER PUBLICATIONS

Y. Park et al., 35 Archives of Pharmacal Research, 1393-1401 (2012) (Year: 2012).*
Y. Han et al., 522 Molecular and Cellular Endocrinology (2021) (Year: 2021).*
Park, Yohan, et al., "N-Methylthioureas as New Agonists of Retinoic Acid Receptor-Related Orphan Receptor", Arch. Pharm. Res., vol. 35, No. 8, pp. 1393-1401 (2012).

* cited by examiner

*Primary Examiner* — Alexander R Pagano
(74) *Attorney, Agent, or Firm* — Servilla Whitney LLC

(57) ABSTRACT

The present disclosure relates to a method for preparing 1-(4-benzyloxy-benzyl)-3-methyl-thiourea and a method for preparing a novel stable crystalline form A of 1-(4-benzyloxy-benzyl)-3-methyl-thiourea.

11 Claims, 3 Drawing Sheets

METHOD FOR PREPARING NOVEL CRYSTALLINE FORMS OF 1-(4-BENZYLOXY-BENZYL)-3-METHYL-THIOUREA

TECHNICAL FIELD

The present disclosure relates to a method for preparing 1-(4-benzyloxy-benzyl)-3-methyl-thiourea compound and a method for preparing a novel stable crystalline form A of the compound.

BACKGROUND ART

RORα, also known as NR1F1, RORA, or RZR, is a member of the steroid hormone receptor superfamily, and a transcriptional factor regulating gene expression. It is known that the activation of the RORα gene is useful for preventing or treating a metabolic disease or inflammatory disease.

Compounds of Formula 1, which activate the RORα gene, are disclosed in Korean Patent No. 10-1450960 and US Patent Publication No. US 2018/0265462.

[Formula 1]

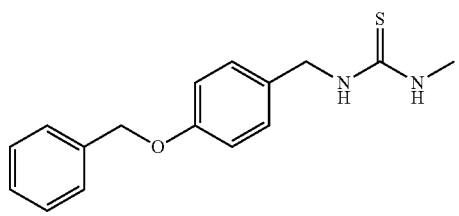

A method for preparing 1-(4-benzyloxy-benzyl)-3-methyl-thiourea (hereinafter, "compound of formula 1") is also described in Korean Patent No. 10-1450960 and US Patent Publication No. US 2018/0265462, which are incorporated herein by reference. Further, they are also disclosed in Arch Pharm Res Vol 35, No 8, 1393-1401, 2012.

A method for preparing the compound of formula 1 comprising the steps of i) reacting the compound of benzaldehyde structure with thionylurea using titanium (IV) catalyst to prepare a reaction intermediate; ii) reacting the reaction intermediate through reductive aminization to prepare the compound of formula 1; and iii) purifying the compound of formula 1 by filtration or column chromatography is disclosed in Korean Patent No. 10-1450960, US Patent Publication No. US 2018/0265462, and Arch Pharm Res Vol 35, No 8, 1393-1401, 2012, as indicated in Reaction Scheme A below.

[Reaction Scheme A]

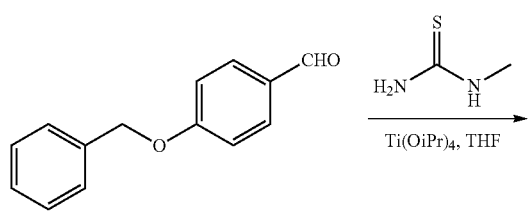

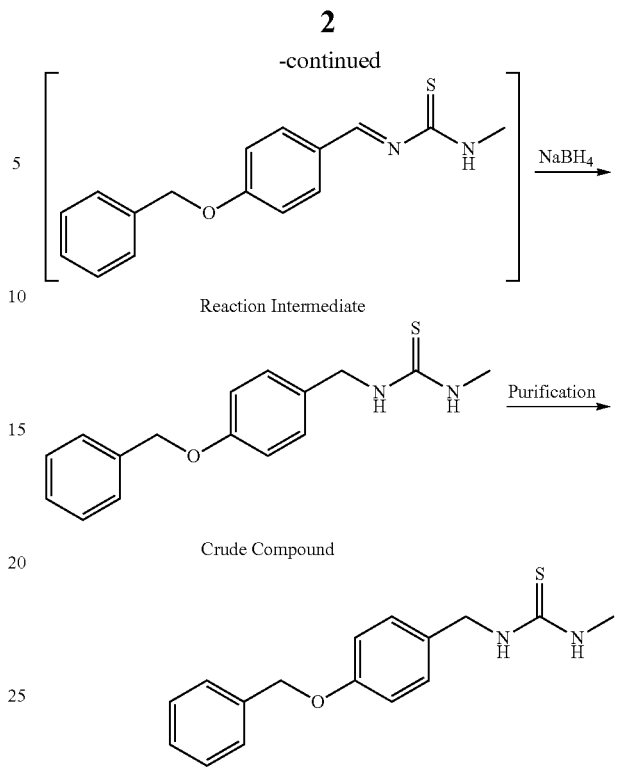

Specifically, in Korean Patent No. 10-1450960 and US Patent Publication No. US 2018/0265462, 4-benzyloxybenzaldehyde and N-methylthionylurea in excess amount were put into a reaction container and dissolved in a tetrahydrofuran solvent. And then, 1.7 equivalent of titanium (IV) isopropoxy oxide was added to synthesize an imine compound, a reaction intermediate, at reflux condition, followed by reacting through a reduction using a sodium borohydride reagent at ambient temperature to synthesize the desired compound of formula 1 in a synthetic yield of 30%.

In addition, it is disclosed in Arch. Pharm. Res. Vol 35, No 8, 1393-1401, 2012 that using Reaction Scheme A that is the same as the method described above, a compound of formula 1 was synthesized, and then, the obtained compound was purified by column chromatography using silica gel to synthesize the compound of formula 1 in a synthetic yield of 30%.

As such, titanium (IV) isopropoxy oxide used in a conventional known method for preparing the compound of formula 1 is an inflammable material, and thus, when exposed to moisture, the reagent is well decomposed and has an influence on a synthetic yield. Further, since a flash point of the reagent is as very low as 45° C., it should be cautiously used and stored. In addition, if the compound prepared using the reagent is used as a pharmaceutical product, it is mandatory to manage a titanium metal rigorously. Generally, this reagent is able to be utilized industrially, but it should be under very strict management in regard to safety and environmental problem and the like, and there may be some difficulties to maintain the quality of the reagent to be used. In order to overcome these difficulties, reactions using various reagents have been tried, but the desired compound could not be synthesized, or the desired compound could not be obtained in a synthetic yield of the desired extent.

In addition, in small scale (in hundreds mg scale), a synthetic yield of Step 1 is as very low as 30%, and a process of column chromatography for purification is not advantageous to utilize in commercial production in terms of economic profits.

On the other hand, crystalline forms of the compound of formula 1 have never been reported before. If the compound of formula 1 is prepared by using the reaction condition mentioned above, it was confirmed that a crystalline form of the compound was not consistent and its stability decreased. According to published guidelines or regulations in each country, there are fundamental requirements that pharmaceutically active ingredients need to meet. For example, stability of a pharmaceutical ingredient, stability during the preparation of a pharmaceutical formulation, and stability of a pharmaceutical substance in a final pharmaceutical composition are considered. There are various factors that affect the stability of a pharmaceutically active ingredient, but it is well known that the crystalline forms of the same active ingredient may have substantially different and pharmaceutically important properties such as an elution and bioavailability, as well as stability. With a view mentioned above, it is considered that it is difficult to utilize the preparation method commercially.

Thus, the present inventors have tried to find the preparation method suitable for a commercial mass production while using a stable and commercially available reagent and also enhancing a synthetic yield. In particular, based on the results of studying a method for preparing the compound of formula 1 in a stable crystalline form, a commercially available and economical and improved preparation method for preparing the compound of formula 1 in a stable crystalline form in a high yield was secured, and it was confirmed that the preparation method is able to be applied to a mass production, and thus, the present invention has been completed.

Technical Problem

Some embodiments of the disclosure provide a method for preparing 1-(4-benzyloxy-benzyl)-3-methyl-thiourea that is commercially available.

Some embodiments of the disclosure provide a method for preparing a stable crystalline form A of 1-(4-benzyloxy-benzyl)-3-methyl-thiourea.

Solution to Problem

The present disclosure relates to a method for preparing 1-(4-benzyloxy-benzyl)-3-methyl-thiourea compound represented by formula 1 and crystalline form A thereof.

In one embodiment, the present disclosure provides a method for preparing the compound of formula 1 in crystalline form A, comprising the steps of i) using a compound of benzaldehyde structure, thionylurea, a silane reagent substituted with one to three alkyl groups, and trifluoroacetic acid to prepare the compound of formula 1; and ii) slurrying or crystallizing the compound of formula 1 to prepare the novel crystalline form A.

Specifically, the above preparation method may be schematized as in Reaction Scheme B below.

[Reaction Scheme B]

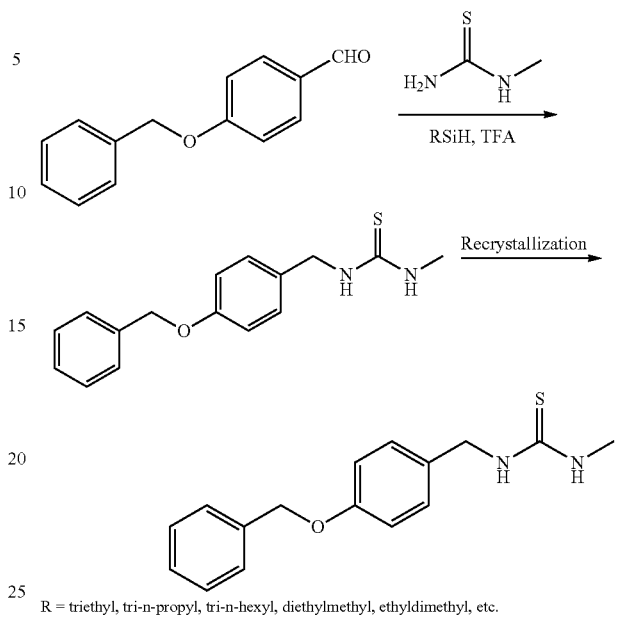

R = triethyl, tri-n-propyl, tri-n-hexyl, diethylmethyl, ethyldimethyl, etc.

Hereinafter, each of steps of the preparation method will be explained in details.

The step i) is a step of reacting 4-(benzyloxy)benzaldehyde with N-methylthiourea in the presence of silane substituted with one to three alkyl groups and trifluoroacetic acid to synthesize the compound of formula 1. Specifically, the step i) is a step of dissolving 4-(benzyloxy)benzaldehyde, N-methylthiourea, and the substituted silane in a reaction solvent, and then, adding trifluoroacetic acid to synthesize the compound of formula 1.

In this case, the substituted silane is a silane ($SiH_4$) group in which one to three hydrogen atoms are substituted with alkyl groups, and for example, may be triethylsilane, tri-n-propylsilane, tri-n-hexylsilane, diethylmethylsilane, and ethyldimethylsilane, but is not limited thereto. Preferably, the substituted silane is triethylsilane. The solvent as used includes tetrahydrofuran, acetone, ethyl acetate, dichloromethane, dimethylformamide, acetonitrile, dimethyl sulfoxide, toluene, and a mixed solvent thereof, but is not limited thereto. Preferably, the reaction solvent is acetonitrile, dichloromethane, or toluene.

The step ii) is a step of slurrying or crystallizing the compound of formula 1 obtained in step i) in a solvent without a column purification process like a conventional technique to obtain a single crystalline form in a high purity. The used solvent may be selected from the group consisting of ethyl acetate, diethyl ether, tetrahydrofuran, acetone, acetonitrile, N-methyl-2-pyrrolidone, methyl t-butyl ether, water, n-heptane, and a mixed solvent thereof. In one embodiment, the solvent used for purification and preparation of crystalline form A is a mixed solvent of acetone and water, a mixed solvent of acetonitrile and water, or a mixed solvent of ethyl acetate and n-heptane. In this case, the used temperature is −20° C. to reflux temperature, preferably 0° C. to 50° C., but is not limited thereto.

In case of 4-(benzyloxy)benzaldehyde used in Reaction Scheme B above, it may be used through commercial purchase, and as a synthesis method, various methods are very well known in WO2007/56366, WO2003/106403, Chemical Communications, 1999, No. 18 p. 1907-1908, Journal of the American Chemical Society, 2004, vol. 126, No. 23 p. 7359-7367, Synlett, 2003, No. 3 p. 377-381 and the like. In one embodiment, 4-(benzyloxy)benzaldehyde may be synthesized by reacting benzyl chloride with 4-hydroxybenzaldehyde under an acetone solvent using potassium carbonate using the same method as in Reaction Scheme C below.

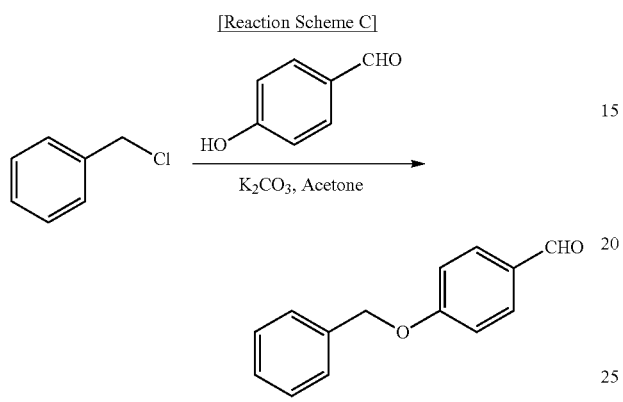

[Reaction Scheme C]

The crystalline form A may exhibit a powder X-ray diffraction (PXRD) spectrum including characteristic peaks at diffraction angles 2θ±0.2° of 19.6, 23.0, 24.4, and 27.4. The powder X-ray diffraction (PXRD) spectrum of crystalline form A may further include characteristic peaks at diffraction angles 2θ±0.2° of 13.4, 15.3, 15.9, and 21.6, in addition to the previously illustrated peaks. In addition, the powder X-ray diffraction (PXRD) spectrum of crystalline form A may further include characteristic peaks at diffraction angles 2θ±0.2° of 10.9, 16.3, 27.0, and 29.4. Alternatively, crystalline form A may exhibit a powder X-ray diffraction (PXRD) spectrum including characteristic peaks at four or more diffraction angles 2θ±0.2° selected from the group consisting of 10.9, 13.4, 15.3, 15.9, 16.3, 19.6, 21.6, 23.0, 24.4, 27.0, 27.4, and 29.4.

It is to be understood that the polymorph exhibits a PXRD pattern having a characteristic peak at a position of a recited diffraction angle 2θ±0.2°, along with the intensity (% (I/I0)) value. It is to be noted that the intensity value is included for information only, and the definition of each peak should not be construed as being limited to a specific intensity value.

Some embodiments of the present disclosure provide a method for preparing 1-(4-benzyloxy-benzyl)-3-methyl-thiourea, in which the preparation processes are very simple, the efficiency of the preparation is augmented, and a yield is largely enhanced. In particular, the present inventors have tried reactions using various reagents through a variety of experiments, but as confirmed from the results of Comparative Example 1 to 4, the desired compound could not be synthesized, or the desired compound could not be obtained in a synthetic yield of the desired extent. On the other hand, if the preparation method of the present disclosure was used, the desired compound could be obtained in a high yield.

In addition, some embodiments of the present disclosure provide a method for preparing 1-(4-benzyloxy-benzyl)-3-methyl-thiourea in novel crystalline form A, which is stable and easy for a mass production.

Figure 1:
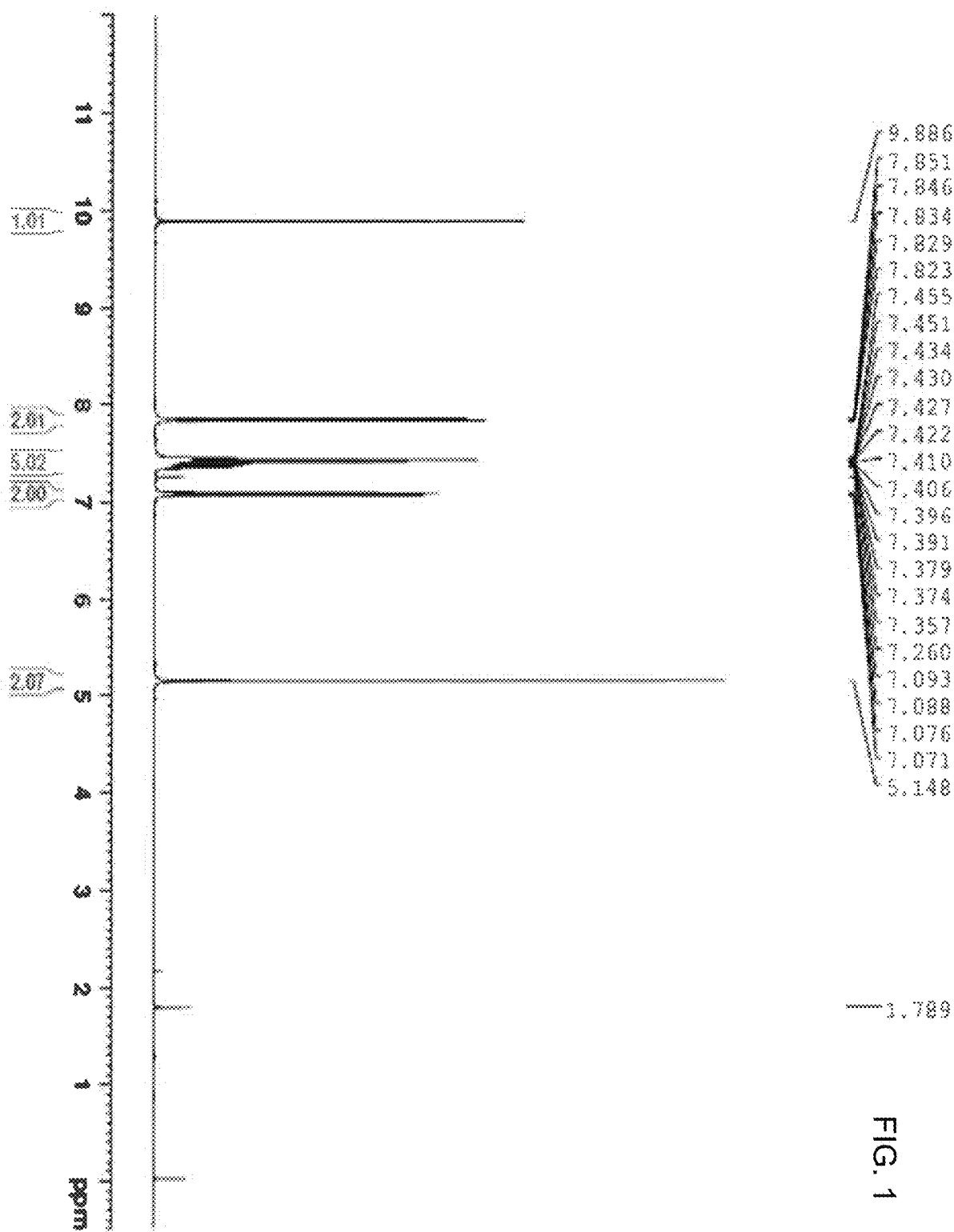
FIG. 1 shows $^1$H-NMR data of 4-(benzyloxy)benzaldehyde.

Hereinafter, embodiments of the present disclosure will be described in more detail through working examples. However, the examples are merely provided for the purpose of illustration of the present disclosure, but are not to be construed as the limitation of the claimed scope. Of course, it will be apparent to those skilled in the art that various changes and modifications can be made within the scope and technical scope of the present disclosure, and such changes and modifications also fall within the scope of the appended claims.

Example 1. Preparation of 4-(benzyloxy)benzaldehyde 4-hydroxybenzaldehyde (20 g) was added to a flask and dissolved in ethyl acetate (100 mL), followed by adding potassium carbonate (47.5 g) and benzylbromide (29.4 g) at ambient temperature. The reaction solution was heated to 60±5° C. and then stirred for 23 hours. After the reaction solution was cooled to 30±5° C., the reaction solution was filtered and concentrated under reduced pressure. The concentrated residue was dissolved in acetone (70 mL), and the reaction solution was heated to 40 to 45° C. After water (210 mL) was added slowly dropwise to the reaction solution, the reaction solution was cooled to 25 to 30° C. and then stirred further for 1 hour. The resulting solid was filtered and then dried to obtain the desired product (31.9 g, yield 92%).

The chemical shifts of $^1$H NMR of the obtained desired product were shown in FIG. 1 and below.

1H NMR (400 MHz, CDCl$_3$) δ 9.89 (s, 1H), 7.85~7.82 (m, 2H), 7.46~7.35 (m, 5H), 7.09~7.07 (m, 2H), 5.15 (s, 2H)

Example 2. Preparation of 1-(4-benzyloxy-benzyl)-3-methyl-thiourea and Crystalline Form A Thereof 1) Step 1: Preparation of 1-(4-benzyloxy-benzyl)-3-methyl-thiourea compound 4-(benzyloxy)benzaldehyde (10 g) and N-methylthiourea (6.3 g) were added to a flask and dissolved in acetonitrile (150 mL). Triethylsilane (16 g) was added to the reaction solution while stirring at ambient temperature. Trifluoroacetic acid (13 g) was added slowly dropwise to the reaction solution through 10 min while maintaining the temperature at 10° C. to 20° C., followed by stirring at 25 to 30° C. for 16 hours. The reaction solution was then cooled to 10° C. to 20° C., adding dichloromethane (200 mL) and water (200 mL), followed by adjusting pH to 8 to 9 using ammonium hydroxide. An organic layer was separated, washed twice with water (20 mL), dehydrated with sodium sulfate, and distilled under reduced pressure to prepare a desired compound.

2) Step 2: Preparation of Crystalline Form A Using ethyl acetate/n-heptane

Ethyl acetate (5 mL) was added into the desired compound prepared in Step 1, followed by adding n-heptane (15 mL) with stirring. The reaction solution was heated to 40° C. to 50° C., stirred for an hour, cooled to 15° C. to 20° C., and further stirred for 30 min. The solid was filtrated and dried at 60° C. for 8 hours to obtain the desired product (11.6 g, yield 86%).

Figure 2:
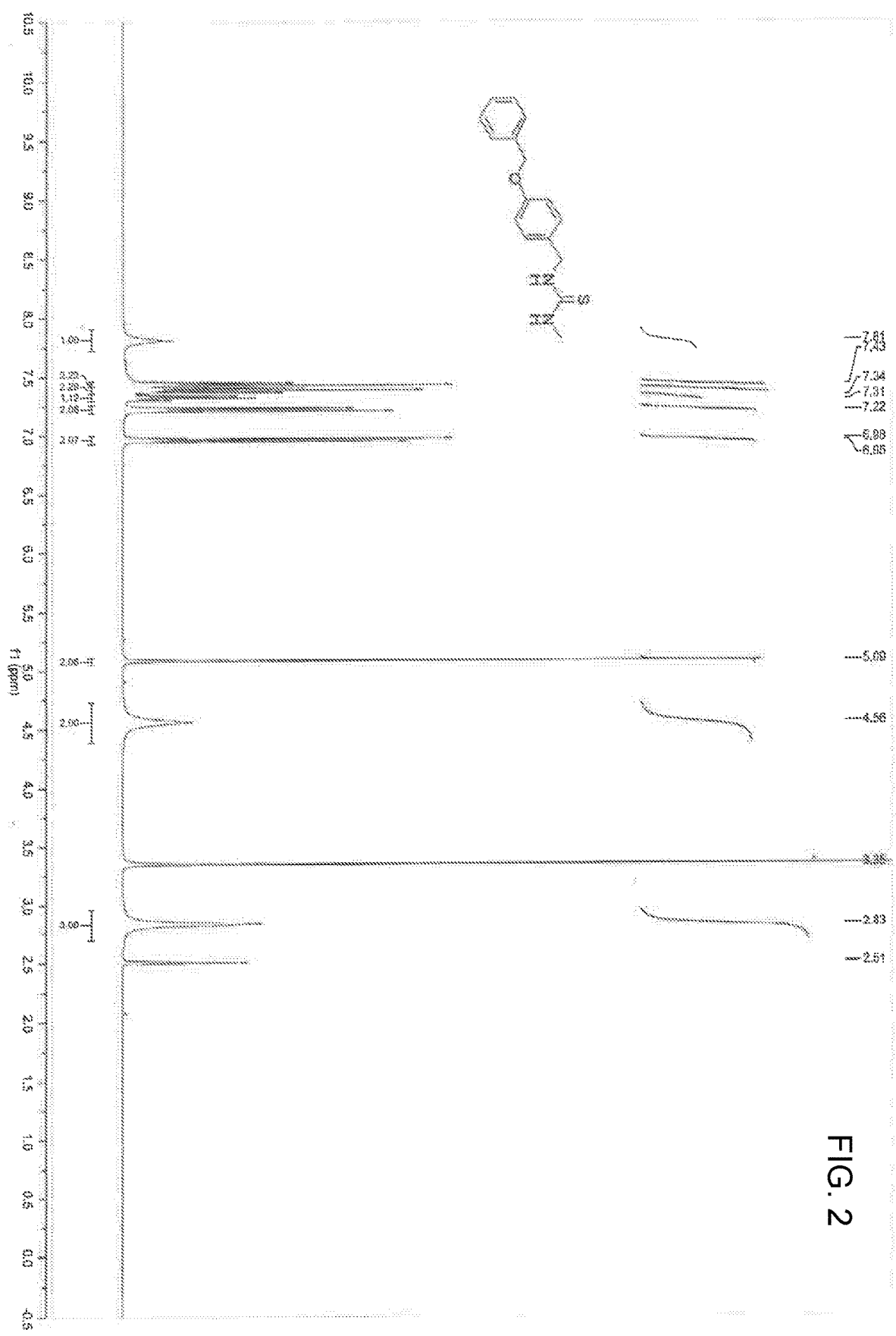
FIG. 2 shows $^1$H-NMR data of 1-(4-benzyloxy-benzyl)-3-methyl-thiourea.

The chemical shifts of $^1$H NMR of the obtained desired product were shown in FIG. 2 and below.

1H NMR (600 MHz, DMSO-d6) δ 7.80 (s, 1H), 7.48~7.26 (m, 5H), 7.25~7.20 (d, 2H), 67.0~6.90 (d, 2H), 5.08 (s, 2H), 4.54 (s, 2H), 2.82 (s, 3H)

Example 3. Preparation of 1-(4-benzyloxy-benzyl)-3-methyl-thiourea and Crystalline Form A Thereof 1) Step 1: Preparation of 1-(4-benzyloxy-benzyl)-3-methyl-thiourea Compound 4-(benzyloxy)benzaldehyde (10 g) and N-methylthiourea (6.0 g) were added to a flask and dissolved in dichloromethane (80 mL). Triethylsilane (16 g) was added to the reaction solution while stirring at ambient temperature. Trifluoroacetic acid (13 g) was added slowly dropwise to the reaction solution through 10 min while maintaining the temperature at 30° C. or less, followed by stirring the reaction solution at 25 to 30° C. for 1 hour. To the reaction solution were added dichloromethane (120 mL) and water (100 mL), followed by adjusting pH to 8 to 9 using ammonium hydroxide. An organic layer was separated, washed with water (100 mL) and then brine (100 mL) sequentially, dehydrated with sodium sulfate, and distilled under reduced pressure to prepare a desired compound.

2) Step 2: Preparation of Crystalline Form A Using ethyl acetate/n-heptane

After ethyl acetate (90 mL) was added into the desired compound prepared in Step 1, the reaction solution was heated to 65 to 75° C., followed by adding slowly dropwise n-heptane (180 mL). The reaction solution was cooled to 20° C. to 30° C. and then stirred further for 1 hour. The solid was filtrated and dried at 45° C. to 55° C. for 8 hours to obtain the desired product (11.8 g, yield 88%).

Example 4. Preparation of 1-(4-benzyloxy-benzyl)-3-methyl-thiourea and Crystalline Form A Thereof 1) Step 1: Preparation of 1-(4-benzyloxy-benzyl)-3-methyl-thiourea Compound After acetonitrile (15 L) was added to a reactor, 4-(benzyloxy)benzaldehyde (1.0 kg), N-methylthiourea (467.2 g), and triethylsilane (1.10 kg) were added and the mixture was stirred for 10 min. Trifluoroacetic acid (806.1 g) was added slowly dropwise to the reaction solution through an hour while maintaining the temperature at 15° C. to 25° C., followed by stirring at 20° C. to 30° C. for 3 hours. Water (20 L) was added slowly dropwise during 30 min while maintaining the temperature at 15° C. to 25° C. The obtained solid was filtrated and washed with water to prepare a desired compound.

2) Step 2: Preparation of Crystalline Form A Using Acetonitrile/Water

Acetonitrile (10 L) and water (20 L) were added to the filtrated cake and stirred at 20° C. to 25° C. for 2 hours. The solid was filtrated and washed with water (4 L) and then methyl t-butyl ether (4 L) sequentially, followed by drying at 60° C. for 24 hours to obtain the desired product (1.12 kg, yield 83%, purity by HPLC 99.5%).

The chemical shifts of $^1$H NMR of the obtained desired product were shown in FIG. 2 and below.

1H NMR (600 MHz, DMSO-d6) δ 7.80 (s, 1H), 7.48~7.26 (m, 5H), 7.25~7.20 (d, 2H), 67.0~6.90 (d, 2H), 5.08 (s, 2H), 4.54 (s, 2H), 2.82 (s, 3H)

Experimental Example 1. Powder X-Ray Diffraction (PXRD) Spectrum

Figure 3:
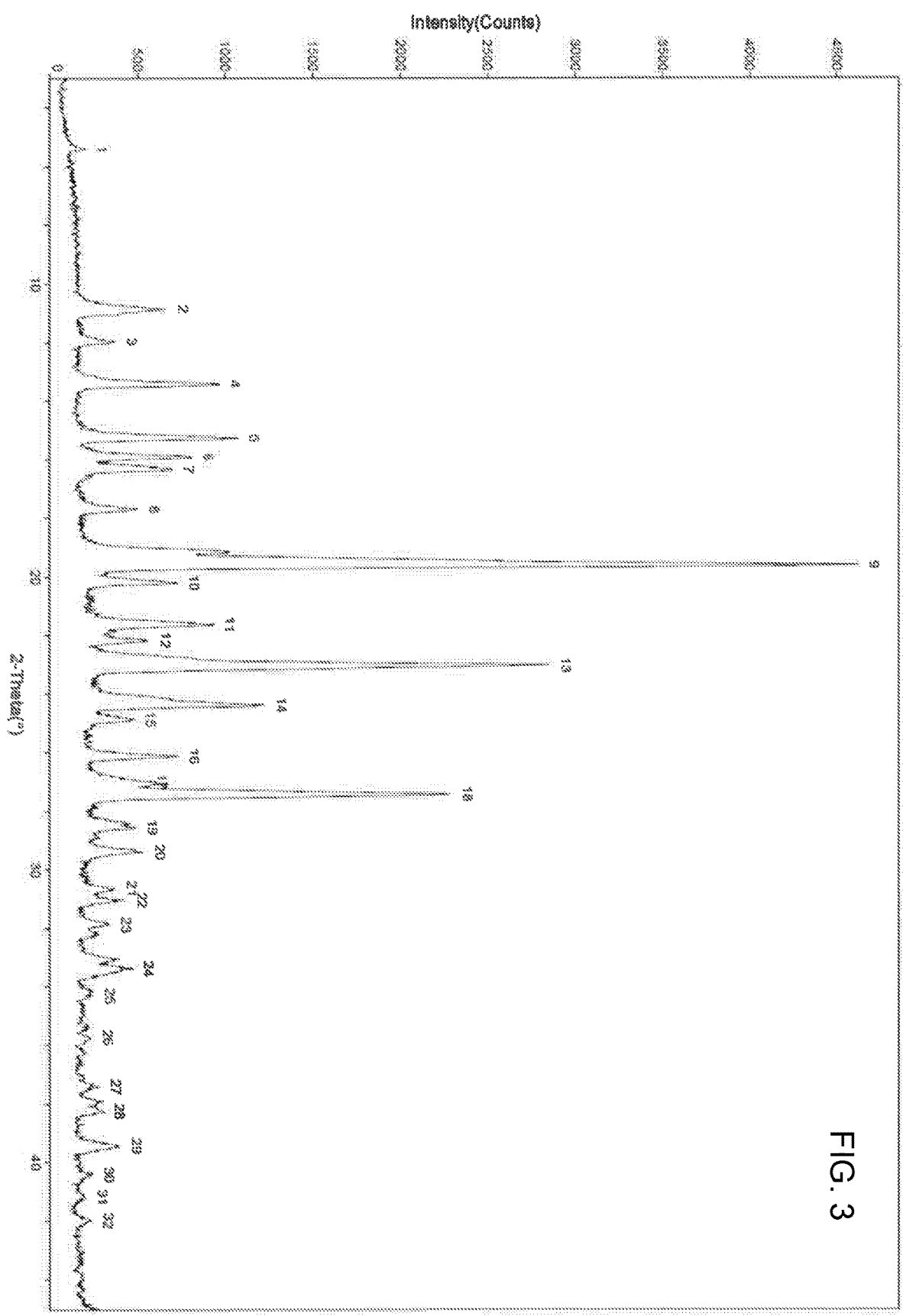
FIG. 3 is a graph illustrating an example of a PXRD pattern of crystalline form A of 1-(4-benzyloxy-benzyl)-3-methyl-thiourea.

The crystalline form A of 1-(4-benzyloxy-benzyl)-3-methyl-thiourea-prepared in the examples was measured by a powder X-ray diffraction device, and representative PXRD spectrum is illustrated in FIG. 3.

As confirmed from FIG. 3, the diffraction angle 2θ values exhibiting a characteristic peak for crystalline form A are as follows.

10.9, 13.4, 15.3, 15.9, 16.3, 19.6, 21.6, 23.0, 24.4, 27.0, 27.4, and 29.4

Comparative Example 1. Preparation of 1-(4-benzyloxy-benzyl)-3-methyl-thiourea Using chlorotrimethylsilane ((CH$_3$)$_3$SiCl)

4-(benzyloxy)benzaldehyde (1.4 g) and N-methylthiourea (0.5 g) were added to a flask and dissolved in acetic acid (10 mL). Chlorotrimethylsilane ((CH$_3$)$_3$SiCl) (1.8 g) was added to the solution while stirring at ambient temperature. The solution was stirred for 20 hours while maintaining the temperature at 15° C. to 30° C. Sodium borohydride (420 mg) was added to the solution and further stirred for 3 hours. Water (50 mL) and dichloromethane (50 mL) was added and stirred for 15 min. An organic layer was separated, washed with water, dried with sodium sulfate, and concentrated under reduced pressure to prepare a crude compound. Ethyl acetate:n-heptane=1:3 was added to the crude compound and stirred for 2 hours. The solid was filtered and dried to obtain the desired compound (280 mg, yield 18%, purity by HPLC 95.1%).

When chlorotrimethylsilane was used, the yield was as low as 18%, so that the desired compound could not be obtained in high synthetic yield.

Comparative Example 2. Preparation of 1-(4-benzyloxy-benzyl)-3-methyl-thiourea Using trifluoroacetic acid 4-(benzyloxy)benzaldehyde (500 mg) and N-methylthiourea (318 mg) were added to a flask and dissolved in methanol (10 mL). Trifluoroacetic acid (260 mg) was added to the solution while stirring at ambient temperature. The solution was stirred for 5 hours while maintaining the temperature at 25° C. to 30° C. Sodium borohydride (178 mg) was added to the solution and further stirred for 3 hours. As a result of confirming the obtained compound, only 4-(benzyloxy)benzyl alcohol which is a by-product was produced.

Comparative Example 3. Preparation of 1-(4-benzyloxy-benzyl)-3-methyl-thiourea Using acetyl chloride 4-(benzyloxy)benzaldehyde (500 mg) and N-methylthiourea (318 mg) were added to a flask and dissolved in tetrahydrofuran (10 mL). Acetyl chloride (256 mg) was added to the solution while stirring at ambient temperature. The solution was stirred for 5 hours while maintaining the temperature at 25° C. to 30° C. Sodium borohydride (178 mg) was added to the solution and further stirred for 3 hours. Water (50 mL) and dichloromethane (50 mL) were added and stirred for 15 min. An organic layer was separated, washed with water, dried with sodium sulfate, and concentrated under reduced pressure to prepare a crude compound. Ethyl acetate:n-heptane=1:3 was added to the crude compound and stirred for 2 hours. The solid was filtered and dried to obtain the desired product (305 mg, yield 45%, purity by HPLC 98.9%).

In the present example, a preparation yield was as low as about 45%, and the desired compound could not be obtained in the desired high synthetic yield.

Comparative Example 4. Preparation of
1-(4-benzyloxy-benzyl)-3-methyl-thiourea Using
tosylic acid 4-(benzyloxy)benzaldehyde (1.0 g) and N-methylthiourea (638 mg) were added to a flask and dissolved in tetrahydrofuran (20 mL). Tosylic acid (800 mg) and 4 Å molecular sieves (100 mg) were added to the solution while stirring at ambient temperature. The solution was stirred for 16 hours while maintaining the temperature at 25° C. to 30° C. Sodium borohydride (178 mg) was added to the solution and further stirred for 5 hours. As a result of confirming the obtained compound, only 4-(benzyloxy)benzyl alcohol which is a by-product was produced.

The invention claimed is:

1. A method for preparing 1-(4-benzyloxy-benzyl)-3-methyl-thiourea compound in crystalline form A comprising the steps of:
 (a) reacting 4-(benzyloxy)benzaldehyde with N-methyl-thiourea in the presence of silane substituted with one to three alkyl, groups and trifluoroacetic acid to obtain 1-(4-benzyloxy-benzyl)-3-methyl-thiourea compound; and
 (b) crystallizing 1-(4-benzyloxy-benzyl)-3-methyl-thiourea compound obtained above in a solvent to obtain crystalline form A,
 characterized in that the crystalline form A exhibits a powder X-ray diffraction (PXRD) spectrum comprising characteristic peaks at four or more diffraction angles 2θ±0.2° selected from the group consisting of 10.9, 13.4, 15.3, 15.9, 16.3, 19.6, 21.6, 23.0, 24.4, 27.0, 27.4, and 29.4.

2. The method for preparing 1-(4-benzyloxy-benzyl)-3-methyl-thiourea compound in crystalline form A according to claim 1, characterized in that the substituted silane is selected from the group consisting of triethylsilane, tri-n-propylsilane, tri-n-hexylsilane, diethylmethylsilane, and ethyldimethylsilane.

3. The method for preparing 1-(4-benzyloxy-benzyl)-3-methyl-thiourea compound in crystalline form A according to claim 1, characterized in that the substituted silane is triethylsilane.

4. The method for preparing 1-(4-benzyloxy-benzyl)-3-methyl-thiourea compound in crystalline form A according to claim 1, characterized in that the solvent in step (b) is selected from the group consisting of ethyl acetate, diethyl ether, tetrahydrofuran, acetone, acetonitrile, N-methyl-2-pyrrolidone, methyl t-butyl ether, water, n-heptane, and a mixed solvent thereof.

5. The method for preparing 1-(4-benzyloxy-benzyl)-3-methyl-thiourea compound in crystalline form A according to claim 1, characterized in that the solvent in step (b) is a mixed solvent of acetone and water, a mixed solvent of acetonitrile and water, or a mixed solvent of ethyl acetate and n-heptane.

6. A method for preparing 1-(4-benzyloxy-benzyl)-3-methyl-thiourea compound, characterized by reacting 4-(benzyloxy)benzaldehyde with N-methylthiourea in the presence of a silane substituted with one to three alkyl groups and trifluoroacetic acid.

7. The method for preparing 1-(4-benzyloxy-benzyl)-3-methyl-thiourea compound according to claim 6, characterized in that the substituted silane is selected from the group consisting of triethylsilane, tri-n-propylsilane, tri-n-hexylsilane, diethylmethylsilane, and ethyldimethylsilane.

8. The method for preparing 1-(4-benzyloxy-benzyl)-3-methyl-thiourea compound according to claim 6, characterized in that the substituted silane is triethylsilane.

9. A method for preparing 1-(4-benzyloxy-benzyl)-3-methyl-thiourea compound comprising the steps of:
 (a) dissolving 4-(benzyloxy)benzaldehyde, N-methylthiourea, and a silane substituted with one to three alkyl groups in a reaction solvent to prepare a mixture; and
 (b) adding trifluoroacetic acid to the mixture.

10. The method for preparing 1-(4-benzyloxy-benzyl)-3-methyl-thiourea compound according to claim 9, characterized in that the reaction solvent is selected from the group consisting of tetrahydrofuran, acetone, ethyl acetate, dimethylformamide, acetonitrile, dichloromethane, dimethyl sulfoxide, toluene, and a mixed solvent thereof.

11. The method for preparing 1-(4-benzyloxy-benzyl)-3-methyl-thiourea compound according to claim 9, characterized in that the reaction solvent is acetonitrile, dichloromethane, or toluene.

* * * * *